(12) United States Patent
Leleti et al.

(10) Patent No.: US 11,299,455 B2
(45) Date of Patent: Apr. 12, 2022

(54) PROCESS FOR DIASTEREOSELECTIVE SYNTHESIS OF VICINAL DIAMINES

(71) Applicant: PIRAMAL PHARMA LIMITED, Mumbai (IN)

(72) Inventors: Rajender Reddy Leleti, Gujarat (IN); Sharadsrikar Kotturi, Gujarat (IN); Kumara Swamy Nalivela, Gujarat (IN); Chirag Patel, Gujarat (IN); Poojabahen Raval, Gujarat (IN); Vinkal Zalavadiya, Gujarat (IN)

(73) Assignee: PIRAMAL PHARMA LIMITED, Mumbai (IN)

( * ) Notice: Subject to any disclaimer, the term of this patent is extended or adjusted under 35 U.S.C. 154(b) by 0 days.

(21) Appl. No.: 17/256,962

(22) PCT Filed: Jul. 11, 2019

(86) PCT No.: PCT/IB2019/055919
§ 371 (c)(1),
(2) Date: Dec. 29, 2020

(87) PCT Pub. No.: WO2020/012403
PCT Pub. Date: Jan. 16, 2020

(65) Prior Publication Data
US 2022/0073454 A1 Mar. 10, 2022

(30) Foreign Application Priority Data
Jul. 12, 2018 (IN) .............................. 201821025994

(51) Int. Cl.
*C07C 303/40* (2006.01)
*C07D 307/52* (2006.01)

(52) U.S. Cl.
CPC .......... *C07C 303/40* (2013.01); *C07D 307/52* (2013.01)

(58) Field of Classification Search
None
See application file for complete search history.

(56) References Cited

FOREIGN PATENT DOCUMENTS

WO    2010/031750 A1    3/2010

OTHER PUBLICATIONS

ISR for International Application No. PCT/IB2019/055919.
Written Opinion for International Application No. PCT/IB2019/055919.
Lingmin Wu, et al., "Synthesis of Trifluoromethyl-Containing Vicinal Diamines by Asymmetric Decarboxylative Mannich Addition Reactions", The Journal of Organic Chemistry, 2015, vol. 80(6), pp. 3187-3194. Reaction A & B in Scheme 2 on p. 3188; compounds 4-7 in Reaction A in Scheme 2 1-6 on p. 3188; compounds 4, 8, 9a & 10a in Reaction B in Scheme 2 on p. 3188 & first and second paragraph of the Results and Discussion section on pp. 3187-3188.
Grazia Piizzi, et al., "Design, Synthesis, and Properties of a Potent Inhibitor of Pseudomonas aeruginosa Deacetylase LpxC", Journal of Medicinal Chemistry, 2017, vol. 60(12), pp. 5002-5014. Compounds 16 & 17 in Scheme 2 on p. 5006 & reagents and conditions for step b in 1-6 Scheme 2 on p. 5006.
Chen Xie, et al., "Concise Asymmetric Synthesis of 13-Tritluoromethylated α,β-Diamino Esters through Addition Reactions of Glycine Esters to CF₃-Sulfinylimine", European Journal of Organic Chemistry, 2014, vol. 2014(7), pp. 1445-1451. Compound 1, 2a & 3a in Table 1 on p. 1446 & Table I on p. 1446, especially entries 2 & 3.
Leleti Rajender Reddy, et al., "Umpolung Synthesis of Vicinal Diamines: Diastereoselective Addition of 2-Azaallyl Anions to Davis-Ellman's Imines", Organic Letters, 2018, vol. 20(17), pp. 5423-5426.

*Primary Examiner* — Samantha L Shterengarts
(74) *Attorney, Agent, or Firm* — Ladas & Parry LLP

(57) ABSTRACT

The present invention relates to an improved process for diastereoselective synthesis of vicinal diamines (1). The process involves highly regio- and diastereoselective addition of 2-azaallyl anions (4) to N-tert-butanesulfinylimines (5) to produce vicinal diamines (1).

6 Claims, No Drawings

PROCESS FOR DIASTEREOSELECTIVE SYNTHESIS OF VICINAL DIAMINES

This application is a national phase entry under 35 USC 371 of International Patent Application No.: PCT/IB2019/055919 filed on 11 Jul. 2019, which claims the benefit of Indian Application No. 201821025994 filed on 12 Jul. 2018, the entire content of which is incorporated by reference.

FIELD OF THE INVENTION

The present invention relates to an improved process for the preparation of diastereoselective synthesis of vicinal diamines of compound of formula (I).

BACKGROUND OF THE INVENTION

The following discussion of the prior art is intended to present the invention in an appropriate technical context, and allows its significance to be properly appreciated. Unless clearly indicated to the contrary, reference to any prior art in this specification should not be construed as an expressed or implied admission that such art is widely known or forms part of common general knowledge in the field.

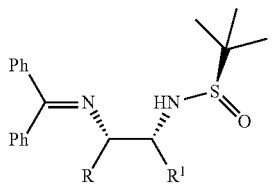

(1)

wherein, R and $R_1$ are independently selected from H, $C_1$-$C_{10}$ linear or branched or cyclic alkyl, substituted or unsubstituted aryl, ester, ether, hetero aryl, halo, haloalkyl.

The vicinal diamine compounds of formula (1) are enantiomerically pure vicinal diamines and are of great importance in organic chemistry because of their presence in many natural products and biologically active compounds as well as utility in organic synthesis.

Moreover, the vicinal diamine compounds of formula (I) are compounds of great relevance in coordination chemistry and asymmetric catalysis by acting as ligands and chiral auxiliaries, resolving agents and precursors of receptors. These utilizations brought about the development of synthetic methods for the preparation of vicinal diamine compounds of formula (1) in enantiomerically pure form. Several processes for the preparation of vicinal diamines are well-known in the art.

Tetrahedron Letters Vol 32, No 8, Pages 5865-5868 (1991) discloses preparation of diastereoselective synthesis of vicinal diamines via the reactions of allylic Grignard reagents with readily available "protected" 1,2-bisimines which is further extended to preparing optically pure diamines by the use of chiral 1,2-bisimine precursors (Refer: Scheme 1).

Scheme-1

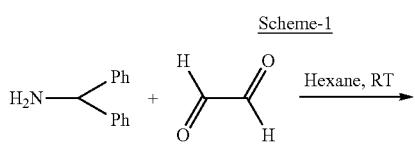

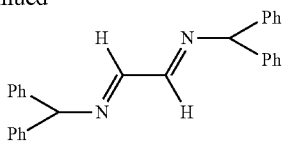

Synlett 18, pp 2776-2780 (2005) depicts the preparation of enantiomerically enriched C2-symmetrical vicinal diamines via addition of organometallic reagents to the carbon-nitrogen double bonds of the chiral bisimine derived from glyoxal (Refer: Scheme 2).

Scheme-2

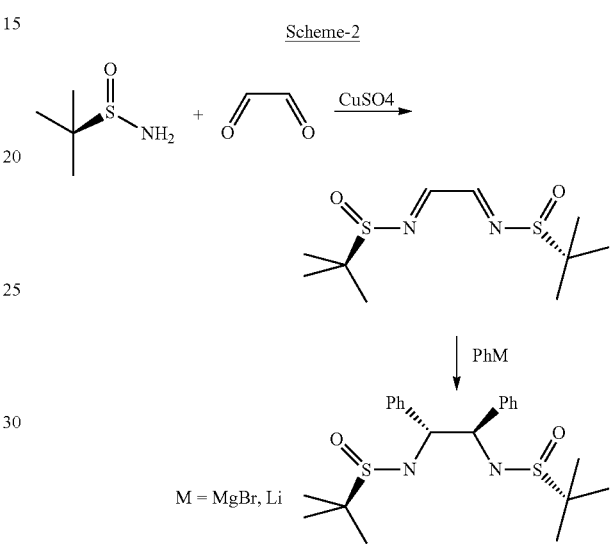

A study of the reported processes for the preparation of vicinal diamines reveals that these processes are associated often with low stereoselectivity. Particularly, Xu et al. have reported an elegant method for asymmetric synthesis of C2-symmetrical vicinal diamines in a highly enantioselective manner by $SmI_2$ catalysed homocoupling of aromatic N-tert-butanesulfinyl imines, but this method is limited to the synthesis of aromatic C2-symmetrical vicinal diamines (Refer: Scheme 3).

Scheme-3

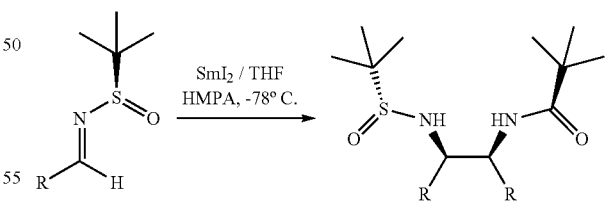

Therefore, a highly efficient asymmetric synthesis of enantiopure vicinal diamines remains a significant synthetic challenge.

Inventors of the present invention have developed an improved process that addresses the problems associated with the processes reported in the prior art. The inventors of the present inventors reported a direct method to access enantiopure vicinal diamines, which is an umpolung approach of 2-azaallyl anions addition to Davis-Ellman's imines which has not been explicitly reported.

Accordingly, the present invention provides a straightforward, scalable and highly diastereoselective method that provides entry to enantioenriched vicinal diamines in high yields with broad substrate scope. The reported method is simple, efficient, cost effective, environmentally friendly and commercially scalable for large scale operations.

SUMMARY OF THE INVENTION

In one aspect, the present invention relates to an improved diastereoselective synthesis of vicinal diamines of compound of formula (1) comprising, reacting compound of formula (2) or compound of formula (3) to produce 2-azaallyl anions (4); and subsequently condensed with compound of formula (5) to produce vicinal diamines (1).

In another aspect, the present invention relates to an improved process for the preparation of diastereoselective synthesis of vicinal diamines of compound of formula (1), (1)

comprising;
(a) reacting a compound of formula (2) or a compound of formula (3) with a base in an organic solvent to produce 2-azaallyl anion of formula (4), which is optionally isolated; and

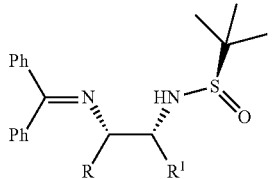
2    3

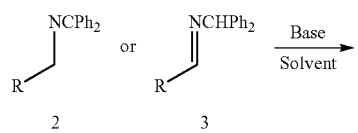
4
2-Azaallyl Anions (b) condensing 2-azaallyl anion of formula (4) with a compound of formula (5) in a solvent to produce vicinal diamines of formula (1).

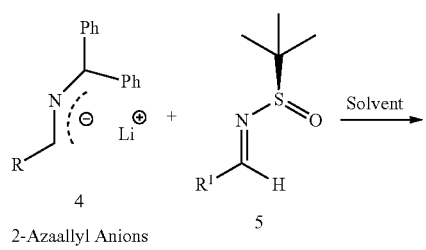
4
2-Azaallyl Anions    5

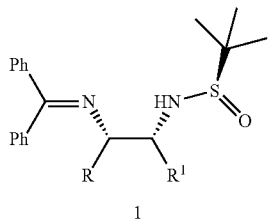
1

DETAILED DESCRIPTION OF THE INVENTION

Accordingly, the present invention relates to an improved process for the preparation of diastereoselective synthesis of vicinal diamines of compound of formula (1), (1)

wherein, R and $R_1$ is independently selected from H, $C_1$-$C_{10}$ linear or branched or cyclic alkyl, substituted or unsubstituted aryl, ester, ether, hetero aryl, halo, haloalkyl.

comprising;
(a) reacting a compound of formula (2) or a compound of formula (3) with a base in an organic solvent to produce 2-azaallyl anion of formula (4), which is optionally isolated; and

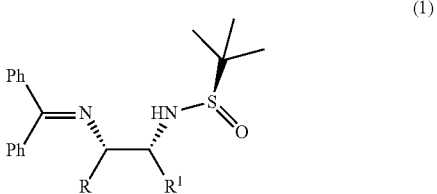
2    3

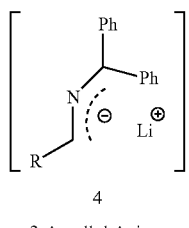
4
2-Azaallyl Anions (b) condensing 2-azaallyl anion of formula (4) with a compound of formula (5) in a solvent to produce vicinal diamines of formula (1).

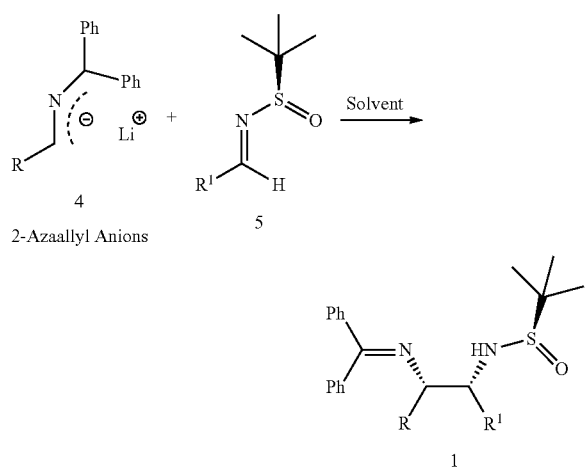

2-Azaallyl Anions

The solvent(s) used in step (a) and (b) is selected from an ether solvent such as tetrahydrofuran, cyclopentyl methyl ether, 2-methyltetrahydrofuran, diethyl ether, dioxane, 1,4-dioxane, 1,2-dioxane and 1,3-dioxane; an alcoholic solvent such as methanol, ethanol, isopropanol, t-amyl alcohol, t-butyl alcohol and hexanol; halogenated solvent such as dichloromethane, 4-bromotoluene, diiodomethane, carbon tetrachloride, chlorobenzene and chloroform; ketone such as acetone; an aprotic solvent such as acetonitrile, N,N-dimethyl formamide (DMF), N,N-dimethyl acetamide, dimethyl sulfoxide (DMSO) and N-methylpyrrolidone (NMP); an aromatic solvent such as toluene, xylene and benzene; water or a mixture thereof.

The base used in step (a) is a strong non-nucleophilic base. Examples of bases suitable for practicing the invention include, but are not limited to, potassium hydride (KH), potassium tert-butoxide (tert-BuOK), sodium amide (NaNH2), sodium hexamethyldisilazide (NaHMDS) and lithium amide bases. In preferred embodiments, the base is a lithium amide base. Examples of lithium amide bases suitable to practice the invention include, but are not limited to, Lithium diethylamide, Lithium diisopropylamide (LDA), Lithium pyrrolidinamide, Lithium piperidinamide, Lithium isopropylcyclohexylamide, Lithium tetramethylpiperidide (LTMP) and lithium hexamethyl disilazide (LiHMDS).

The step (a) is carried out at temperature in the range of −70° C. to −90° C. Most preferably, the temperature is about −78° C.

In the context of the present invention, the term "optionally" when used in reference to any element; including a process step e.g. isolation of a compound; it is intended to mean that the subject element is isolated, or alternatively, is not isolated before transformation into the further compound. Both alternatives are intended to be within the scope of the present invention.

The product formed in step (a) can be used in the next stage with or without isolation of the product.

The inventors of the instant invention developed an efficient, highly regio-, and diastereoselective addition of 2-azaallyl anions to Davis-Ellman's Imines with broad substrate scope, which has not been explicitly reported in the art on the currently considered chemical moieties. This method is found to be very efficient for the preparation of enantiomerically and diastereomerically pure vicinal diamines bearing two adjacent stereo centers.

In order to study reaction conditions, the inventors of the present invention chose the benzophenone-derived imine 2° C. as the model substrate. On carrying out treatment of 2a with NaHMDS in THF at 0° C. for 1 h and followed by addition of N-tert-butanesulfinyl aldimine 5a at 0° C. for 3 h, no reaction was observed. A survey of bases of sufficient strength to deprotonate 2 and form the 2-azaallyl anion 4a revealed the critical role Li plays in promoting the desired reaction (Refer: Table 1), suggesting that Li may also act as a Lewis acid to activate the N-tert-butanesulfinyl imines for attack. Regardless of the tautomer's of imine (2a or 3a), they efficiently undergo deprotonation with LiHMDS under the optimized conditions leading to the same resonance stabilized 2-azaallyl anion 4a, followed by addition to N-tert-butanesulfinyl aldimine 5a in THF at −78° C. for 3 h. The reaction afforded vicinal diamine 1a in 93% yield and with a high diastereomeric ratio (dr 98:2:0:0). The diastereoselectivity of the reaction was determined to be 98:2:0:0 by 1H NMR analysis of the crude product.

The process of the present invention as per the specific embodiment described above is illustrated in Scheme 4.

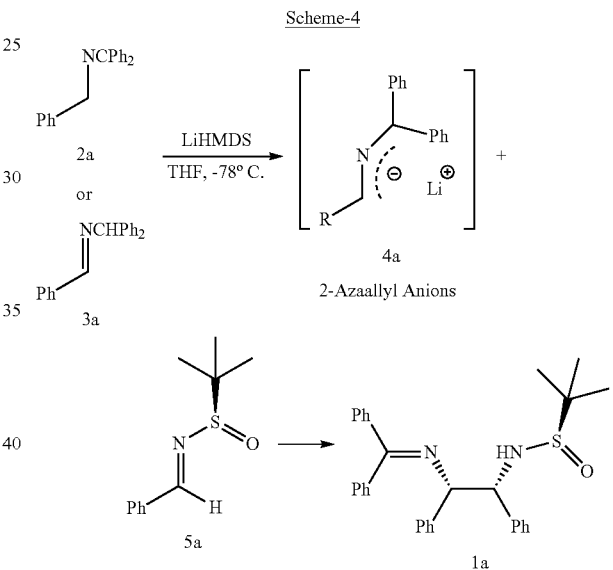

Scheme-4

TABLE-1

Study of reaction conditions and role of lithium[a]

| Substrate/Starting Material (1a or 2a) | Base | Temperature | yield (%)[b] | dr[c] |
|---|---|---|---|---|
| 1a | NaHMDS | −78° C. | 0 | — |
| 1a | NaHMDS | 0° C. | 0 | — |
| 1a | KHMDS | 0° C. | 0 | — |
| 1a[d] | LiHMDS | 0° C. | 90 | 52:48:0:0 |
| 1a[d] | LiHMDS | 0° C. | 91 | 52:48:0:0 |
| 1a | LiHMDS | 0° C. | 93 | 98:2:0:0 |
| 2a | LiHMDS | −78° C. | 92 | 98:2:0:0 |
| 1a | LDA | −78° C. | 55 | 98:2:0:0 |
| 1a | LiTMP | −78° C. | 39 | 98:2:0:0 |

[a]All of the reactions were performed with 2.0 equiv of 1 or 2, 1.8 equiv of base and 1.0 equiv of 4 at −78° C. for 3 h.
[b]Isolated yield.
[c]The diastereoselectivity was determined by 1H NMR analysis of crude product.
[d]DMPU (1.8 equiv) used.

Further, to broaden the scope of this invention, inventors investigated the reaction of azaallyl anion 4a with other N-tert-butanesulfinyl aldimine which eventually leads to the formation of vicinal diamines such as 5b-5e (Table 2) in excellent yields (86-92%) and with high diastereomeric ratios (dr, 90:10:0:0-98:2:0:0).

This unexpected result led to studying the reaction for other substituted azaallyl anions 4. Treatment of p-chlorophenyl substituted azaallyl anion 4b with several substituted N-tert-butanesulfinyl aldimines such as aromatic (5a), hetereoaromatic (5c and thiofurfuryl, 5d) and aliphatic (5e and 5f) derivatives afforded corresponding vicinal diamine 1f-1j (Table 2, entries 6-10) in high yields (85-94%) and with excellent diastereomeric ratios (dr, 90:10:0:0-98:2:0:0).

In the similar way, the reaction of o-chlorophenyl substituted azaallyl anion 4c smoothly reacted with several substituted N-tert-butanesulfinyl aldimines such as aromatic (5a and 5b), hetereoar-omatic (5c and 5d) and aliphatic (5e and 5f) derivatives afforded corresponding vicinal diamines 1k-1p (Table 2, entries 11-16) in excellent yields (85-94%) and with excellent diastereomeric ratios (dr, 90:10:0:0-98:2:0:0). Likewise, p-bromophenyl substituted azaallyl anion 4d reacted with 5c, 5d and 5e to afford the corresponding vicinal diamines 1q, 1r and 1s in 90%, 91% and 84% yield (dr 98:2:0:0, 98:2:0:0, and 90:10:0:0), respectively (Table 2, entries 17-19). The p-flourophenyl substituted azaallyl anion 4e also reacted with 5e to form vicinal amine 1t in 85% yield with dr 92:8:0:0 (Table 2, entry 20).

The process of the present invention as per the specific embodiment described above is illustrated in the Scheme 5.

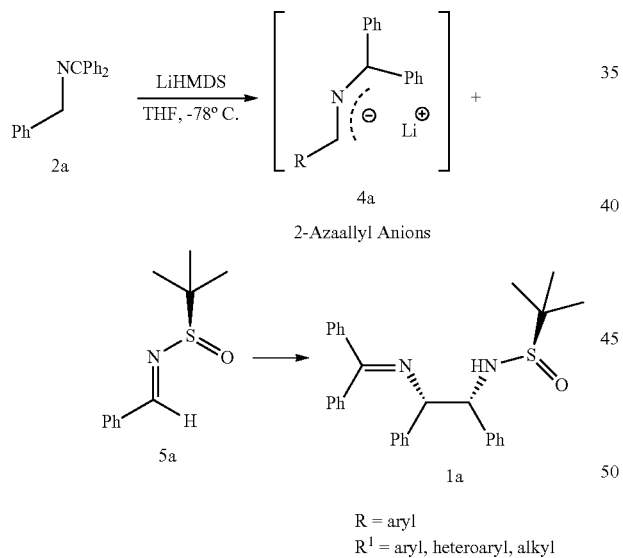

Scheme-5

2-Azaallyl Anions

R = aryl
R$^1$ = aryl, heteroaryl, alkyl

TABLE-2

Azaallyl anion addition to various N-tert-butanesulfinyl aldimine[a, b, c]

| Substrate/Starting material (2a)(R) | Safinamide (5a) (R$^1$) | Vicinal diamine | yield (%)[b] | dr[c] |
|---|---|---|---|---|
| 2a = Phenyl (Ph) | 5a = Phenyl (Ph) | 1a | 93 | 98:2:0:0 |
| 2a = Phenyl (Ph) | 5b = p-methoxy | 1b | 86 | 97:2:0:0 |
| 2a = Phenyl (Ph) | 5c = Furfuryl | 1c | 89 | 97:3:0:0 |
| 2a = Phenyl (Ph) | 5d = Isopropyl | 1d | 92 | 96:2:0:0 |
| 2a = Phenyl (Ph) | 5e = Cyclohexyl | 1e | 88 | 92:8:0:0 |
| 2b = p-chlorophenyl | 5a = Phenyl (Ph) | 1f | 93 | 98:2:0:0 |
| 2b = p-chlorophenyl | 5c = Furfuryl | 1g | 94 | 98:2:0:0 |
| 2b = p-chlorophenyl | 5h = Thiofurfuryl | 1h | 89 | 94:6:0:0 |
| 2b = p-chlorophenyl | 5d = Isopropyl | 1i | 87 | 91:9:0:0 |
| 2b = p-chlorophenyl | 5e = Cyclohexyl | 1j | 85 | 90:10:0:0 |
| 2c = o-chlorophenyl | 5a = Phenyl (Ph) | 1k | 86 | 91:9:0:0 |
| 2c = o-chlorophenyl | 5b = p-methoxy | 1l | 88 | 92:8:0:0 |
| 2c = o-chlorophenyl | 5c = Furfuryl | 1m | 92 | 98:2:0:0 |
| 2c = o-chlorophenyl | 5f = Thiofurfuryl | 1n | 90 | 98:2:0:0 |
| 2c = o-chlorophenyl | 5d = Isopropyl | 1o | 93 | 98:2:0:0 |
| 2c = o-chlorophenyl | 5e = Cyclohexyl | 1p | 93 | 98:2:0:0 |
| 2d = p-bromophenyl | 5c = Furfuryl | 1q | 90 | 98:2:0:0 |
| 2d = p-bromophenyl | 5f = Thiofurfuryl | 1r | 91 | 98:2:0:0 |
| 2d = p-bromophenyl | 5d = Isopropyl | 1s | 84 | 90:10:0:0 |
| 2d = p-flourophenyl | 5d = Isopropyl | 1t | 85 | 92:8:0:0 |

[a]All of the reactions were performed with 2.0 equiv of 1, 1.8 equiv of base and 1.0 equiv of 4 at −78° C. for 3 h.
[b]Isolated yield.
[c]The diastereoselectivity was determined by 1H NMR analysis of crude product.

The representative structures of vicinal diamines 1a to 1t is shown below:

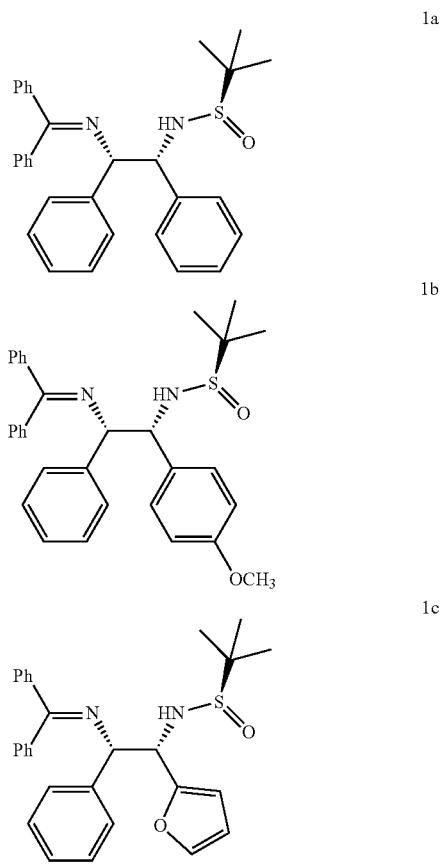

1d
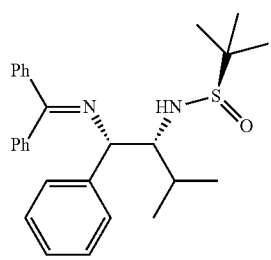
1e
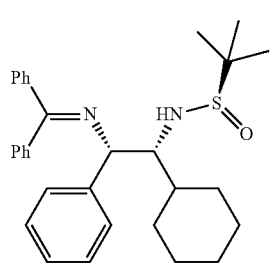
1f
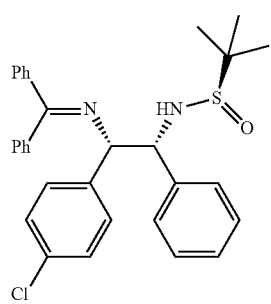
1g
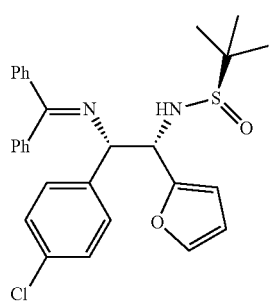
1h
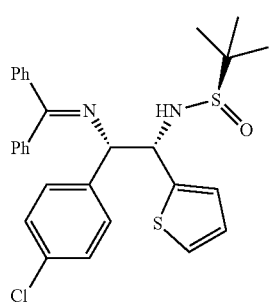
1i
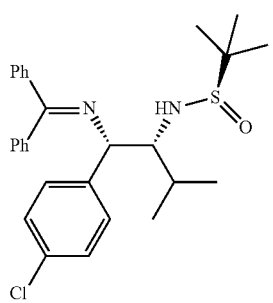
1j
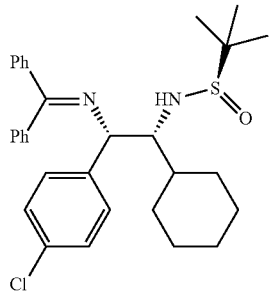
1k
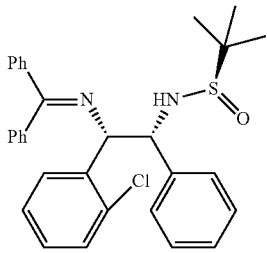
1l
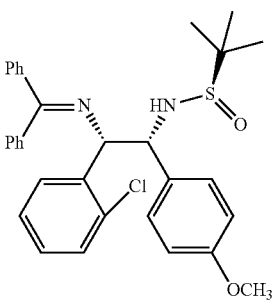
1m
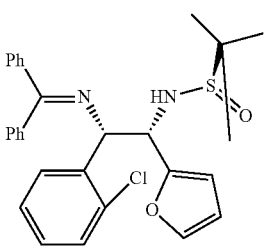

1n

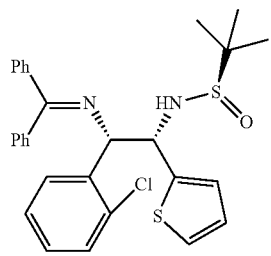

1o

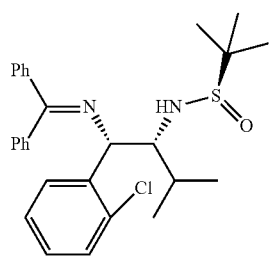

1p

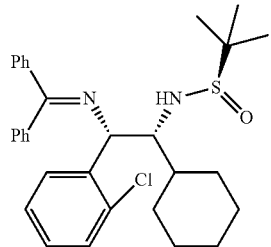

1q

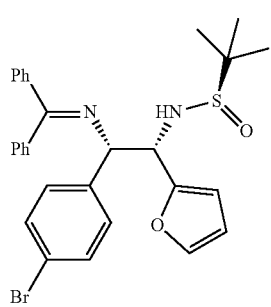

1r

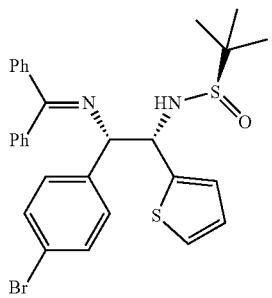

1s

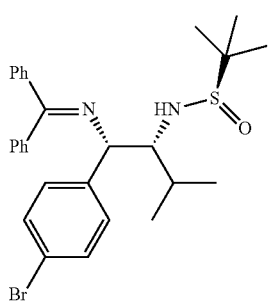

1t

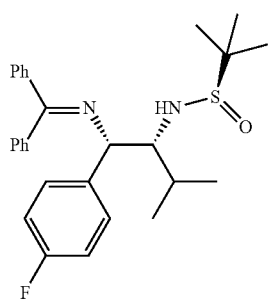

It is evident that, the present invention describes an efficient, highly regio, and diastereoselective addition of 2-azaallyl anions to Davis-Ellman's Imines with broad substrate scope. This method is found to be very efficient for the preparation of enantiomerically and diastereomerically pure vicinal diamines bearing two adjacent stereo centers.

An advantage of this invention is that selective deprotection of the two protected amines (benzophenone imine and sulfinamide) provides versatile synthetic potential in industrial applications as indicated in scheme 6.

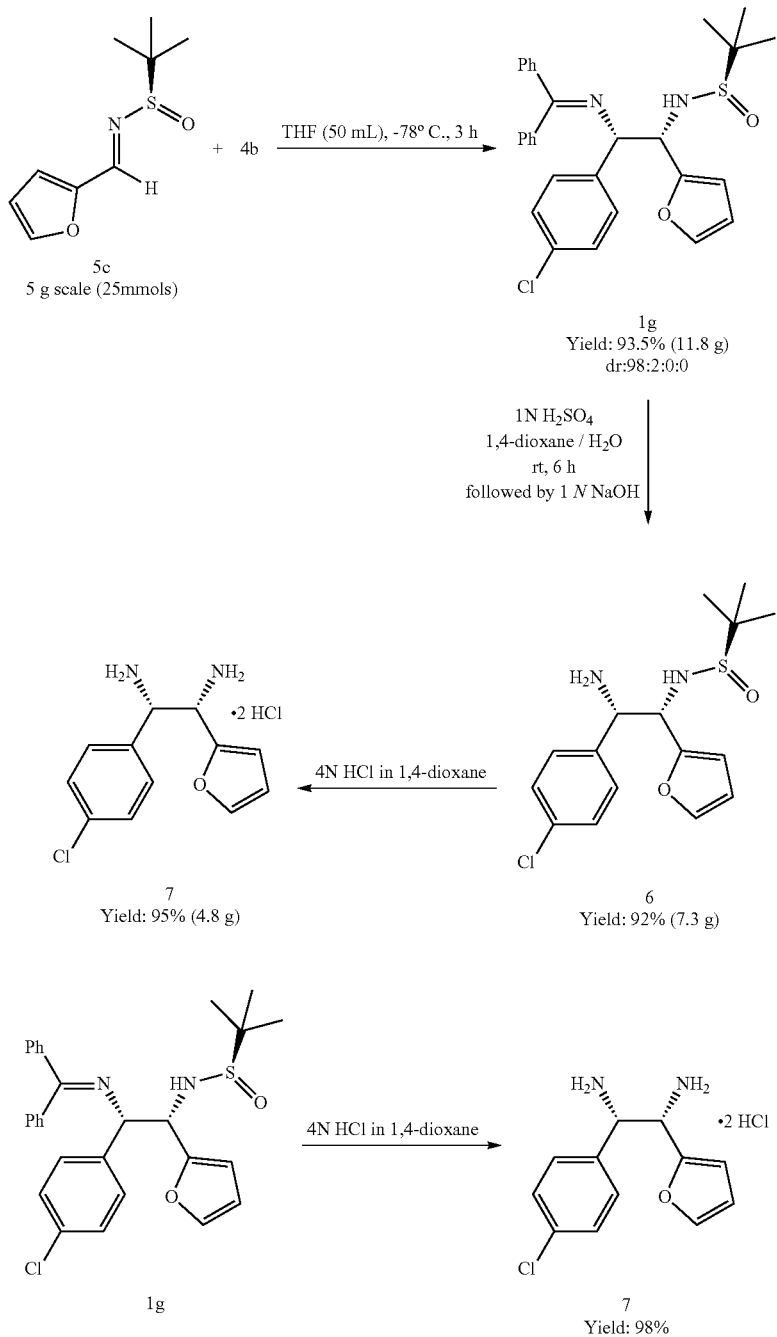

Scheme-6

These differentially protected amines within the products and selective deprotection will facilitate versatile synthetic potential in the industrial application.

The invention is further illustrated by the following examples which are provided to be exemplary of the invention, and do not limit the scope of the invention. While the present invention has been described in terms of its specific embodiments, certain modifications and equivalents will be apparent to those skilled in the art and are intended to be included within the scope of the present invention.

EXAMPLES

General Procedure:

To a solution of Ketimine (2.0 mmol) in anhydrous THF (4.0 ml) was added LiHMDS (1.0 M in THF, 1.8 mmol) at −78° C. under a $N_2$ atmosphere. After 15 min stirring, the sulfinamide (1.0 mmol) was added dropwise in dry THF (2.0 ml) solution for 15 min. The reaction mixture was stirred for 3.0 h at −78° C. Reaction was monitored by TLC then quenched with water (5.0 V) slowly at −78° C. and warmed to room temperature, extracted with EtOAc (3×5 V). The combined organic extracts were dried (Na$_2$SO$_4$) and the solvent concentrated in vacuo. The crude product was purified by column chromatography (1:3, EtOAc/hexane) to obtain the title product (vicinal diamines).

Example 1

(R)-N-((1R,2S)-2-((diphenylmethylene)amino)-1,2-diphenylethyl)-2-methylpropane-2-sulfinamide (1a)

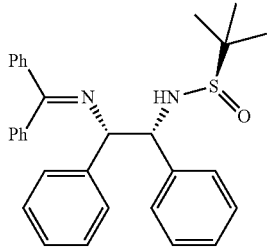 [SMILES: CC(C)(C)[S@@](=O)N[C@H](c1ccccc1)[C@@H](N=C(c1ccccc1)c1ccccc1)c1ccccc1]

Obtained 1a as a white solid (350 mg, 76%) according to the general experimental procedure as described above using N-tert-butanesulfinyl aldimine (R$_S$) 5a (200 mg, 0.95 mmol), Ketimine 2a (1.91 mmol) and LiHMDS (1.0 M in THF, 1.72 mmol).

Melting point=120-122° C., $[\alpha]_D^{25}$=108.57 (c. 0.25, CHCl$_3$), $^1$H-NMR: (400 MHz, DMSO-d$_6$) δ 7.62 (d, J=7.2 Hz, 2H), 7.47-7.17 (m, 18H), 6.35 (d, J=7.2 Hz, 2H), 5.34 (d, J=10.0 Hz, 1H), 4.76 (dd, J=9.6, 4.0 Hz, 1H), 4.57 (d, J=4.0 Hz, 1H), 0.90 (s, 9H). $^{13}$C NMR (100 MHz, DMSO-d$_6$) δ ppm: 168.6, 142.3, 139.2, 136.0, 130.8, 128.8, 128.6, 128.4, 128.2, 128.0, 127.6, 127.3, 127.2, 127.0, 71.3, 66.9, 56.2, 22.5.

Example 2

(R)-N-((1R,2S)-2-((diphenylmethylene)amino)-1-(4-methoxyphenyl)-2-phenylethyl)-2-methylpropane-2-sulfinamide (1b)

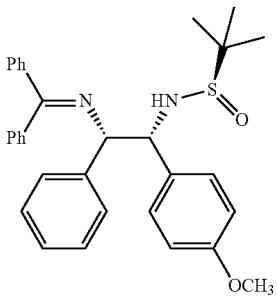 [SMILES: COc1ccc([C@@H](N[S@](=O)C(C)(C)C)[C@@H](N=C(c2ccccc2)c2ccccc2)c2ccccc2)cc1]

Obtained 1b as an off-white solid (320 mg, 75%) according to the general experimental procedure as described above using N-tert-butanesulfinyl aldimine (R$_S$) 5b (200 mg, 0.83 mmol), Ketimine 2a (1.67 mmol) and LiHMDS (1.0 M in THF, 1.5 mmol).

Melting Point=56-58° C., $[\alpha]_D^{25}$=59.53 (c. 0.25, CHCl$_3$)

$^1$H-NMR: (400 MHz, DMSO-d$_6$) δ 7.62-7.15 (m, 15H), 6.77 (d, J=8.4 Hz, 2H), 6.45 (d, J=7.2 Hz, 2H), 5.23 (d, J=9.6 HZ, 1H), 4.70 (dd, J=9.2, 4.4 HZ, 1H), 4.54 (d, J=4.4 Hz, 1H) 3.70 (s, 3H), 0.9 (s, 9H).

$^{13}$C NMR (100 MHz, DMSO-d$_6$) δ ppm: 168.4, 158.6, 142.4, 139.3, 136.1, 134.3, 130.8, 130.1, 129.3, 128.9, 128.7, 128.6, 128.3, 127.7, 127.2, 113.4, 71.5, 66.5, 56.1, 55.5, 22.5.

Example 3

(R)-N-((1S,2S)-2-(4-chlorophenyl)-2-((diphenylmethylene)amino)-1-(furan-2-yl)ethyl)-2-methylpropane-2-sulfinamide (1g)

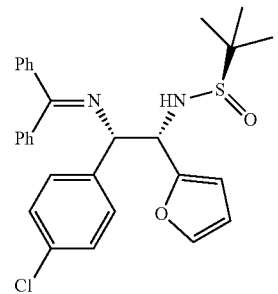 [SMILES: CC(C)(C)[S@@](=O)N[C@H](c1ccco1)[C@@H](N=C(c1ccccc1)c1ccccc1)c1ccc(Cl)cc1]

Obtained 1g as an off-white solid (450 mg, 90%) according to the general experimental procedure as described above using N-tert-butanesulfinyl aldimine (R$_S$) 5c (200 mg, 0.99 mmol), Ketimine 1b (1.98 mmol) and LiHMDS (1.0 M in THF, 1.78 mmol).

Melting Point=110-112° C., $[\alpha]_D^{25}$=66.49 (c. 0.25, CHCl$_3$), $^1$H-NMR: (400 MHz, DMSO-d$_6$) δ 7.64 (d, J=7.2 Hz, 2H), 7.50-7.40 (m, 8H), 7.33 (d, J=8.4 Hz, 2H), 7.22 (d, J=8.4 Hz, 2H), 6.74 (d, J=5.6 Hz, 2H), 6.33 (s, 1H), 5.12 (d, J=9.6 Hz, 1H), 4.58 (d, J=5.2 Hz, 1H), 0.93 (s, 9H).

$^{13}$C NMR (100 MHz, DMSO-d$_6$) δ ppm: 168.7, 143.1, 141.3, 140.7, 139.3, 136.1, 131.7, 130.9, 129.7, 129.1, 128.9, 128.7, 128.7, 128.4, 127.3, 126.8, 110.7, 70.1, 59.5, 56.1, 40.6, 40.4, 40.2, 39.9, 39.7, 39.5, 39.3, 22.6.

Example 4

(R)-N-((1R,2S)-2-(2-chlorophenyl)-1-cyclohexyl-2-((diphenylmethylene) amino)ethyl)-2-methylpropane-2-sulfinamide (1p)

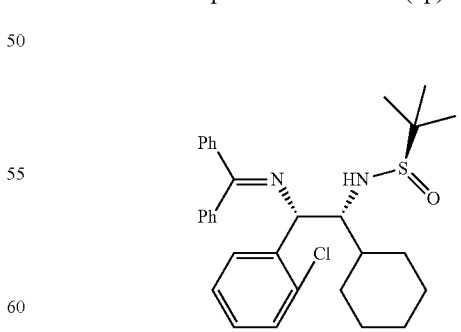

Obtained 1p as pale yellow solid (350 mg, 72%) according to the general experimental procedure as described above using N-tert-butanesulfinyl aldimine (R$_S$) 5e (200 mg, 0.93 mmol), Ketimine 2c (1.86 mmol) and LiHMDS (1.0 M in THF, 1.67 mmol).

Melting Point=142-144° C.,

[α]$_D^{25}$=−84.41 (c. 0.25, CHCl$_3$), $^1$H-NMR: (400 MHz, DMSO-d$_6$) δ 7.69 (d, J=7.2 Hz, 2H), 7.52-7.22 (m, 10H), 6.82 (d, J=6.4 Hz, 2H), 4.93 (d, J=2.0 Hz, 1H), 4.81 (d, J=10.0 Hz, 1H), 3.32 (m, 1H), 2.00-1.00 (m, 11H), 0.95 (s, 9H).

$^{13}$C NMR (100 MHz, DMSO-d$_6$) δ ppm: 168.6, 142.3, 139.2, 136.0, 130.8, 128.9, 128.6, 128.4, 128.2, 128.0, 127.6, 127.3, 127.2, 127.0, 71.3, 66.9, 56.2, 22.5

Example 5

(R)-N-((1S,2R)-1-(4-bromophenyl)-1-((diphenylmethylene)amino)-3-methylbutan-2-yl)-2-methylpropane-2-sulfinamide (1s)

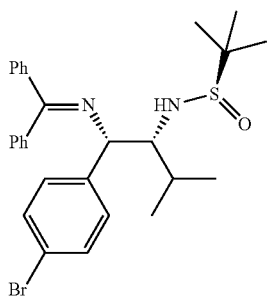

Obtained 1s as an off-white solid (410 mg, 68%) according to the general experimental procedure as described above using N-tert-butanesulfinyl aldimine (R$_S$) 5d (200 mg, 1.14 mmol), Ketimine 2d (2.28 mmol) and LiHMDS (1.0 M in THF, 2.05 mmol).

Melting Point=100-102° C., [α]$_D^{25}$=67.93 (c. 0.25, CHCl$_3$), $^1$H-NMR: (400 MHz, DMSO-d$_6$) δ 7.4 (d, J=6.8 Hz, 2H), 7.49-7.41 (m, 8H), 7.10 (d, J=8.4 Hz, 2H), 6.94 (d, J=4.0 Hz, 2H), 4.58 (d, J=9.2 Hz, 1H), 4.50 (d, J=4.0 Hz, 1H), 3.41-3.38 (m, 1H), 1.68-1.63 (m, 1H), 0.91 (s, 9H), 0.86 (d, J=6.8 Hz, 6H).

$^{13}$C NMR (100 MHz, DMSO-d$_6$) δ ppm: 168.3, 143.2, 139.4, 136.1, 131.5, 130.9, 129.8, 129.3, 128.9, 128.7, 128.7, 127.5, 120.1, 68.8, 67.3, 56.0, 31.3, 22.8, 20.3, 18.8.

Example 6

(1S,2S)-1-(4-chlorophenyl)-2-(furan-2-yl)ethane-1,2-diamine (7)

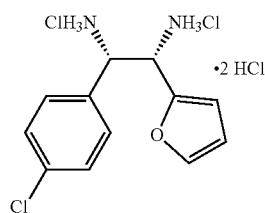

A starting material 1g (500 mg, 0.99 mmol) was dissolved 4 M HCl in 1,4-dioxane (10.0 V) and stirred at room temperature for 16 h. Upon completion of reaction, solvent was removed completely under reduced pressure and washed with ethyl acetate (5.0 V), dried to obtain 7 as a white solid (300 mg, 98%). Melting Point=less than 250° C.

[α]$_D^{25}$=10.40 (c. 0.25, H$_2$O), $^1$H-NMR: (400 MHz, D$_2$O) δ 7.51 (s, 1H), 7.42 (s, 1H), 7.39 (d, 8.4 Hz, 2H), 7.19 (d, 8.4 Hz, 2H), 6.14 (s, 1H), 4.98 (d, J=7.2 Hz, 1H), 4.85 (d, J=6.8 Hz, 1H). $^{13}$C NMR (100 MHz, D$_2$O) δ ppm: 145.0, 143.3, 136.0, 129.7, 129.4, 128.7, 114.9, 108.5, 55.2, 48.8.

Example 7

(R)-N-((1S,2S)-2-amino-2-(4-chlorophenyl)-1-(furan-2-yl)ethyl)-2-methylpropane-2-sulfinamide (6)

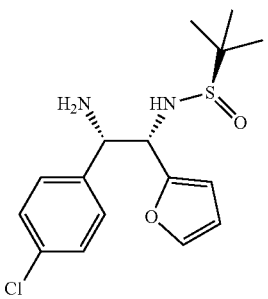 [SMILES: CC(C)(C)[S@@](=O)N[C@H](c1ccco1)[C@@H](N)c1ccc(Cl)cc1]

To a solution of starting material (7) (200 mg, 0.39 mmol) in 1,4-dioxane (10.0 V) was added H$_2$SO$_4$ (1.0 M, 10.0 V) at room temperature and stirred for 6.0 h. Upon completion of reaction, diluted with water (5.0 V) and basified till pH 10 using NaOH solution and extracted with ethyl acetate (10.0 V×3). Organic solvent was dried on Na$_2$SO$_4$ and removed completely under reduced pressure to obtain 6 as an off-white solid (124 mg, 92%). Melting Point=114-116° C.,

[α]$_D^{25}$=11.20 (c. 0.25, CHCl$_3$), $^1$H-NMR: (400 MHz, DMSO-d$_6$) δ 7.53 (s, 1H), 7.46 (s, 1H), 7.36-7.30 (m, 4H), 6.50 (s, 1H), 5.34 (d, 9.2 Hz, 1H), 4.27 (d, J=6.8 Hz, 1H), 4.20 (d, J=6.4 Hz, 1H), 1.00 (s, 9H).

$^{13}$C NMR (100 MHz, DMSO-d$_6$) δ ppm: 143.3, 142.8, 141.1, 131.5, 129.8, 128.1, 126.6, 110.8, 59.9, 59.3, 56.2, 22.9.

We claim:

1. A process for the preparation of diastereoselective synthesis of vicinal diamines of compound of formula (1),

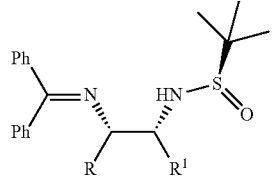

(1)

the process comprising:

(a) reacting a compound of formula (2) or a compound of formula (3) with a base in an organic solvent to produce 2-azaallyl anion of formula (4), which is optionally isolated; and

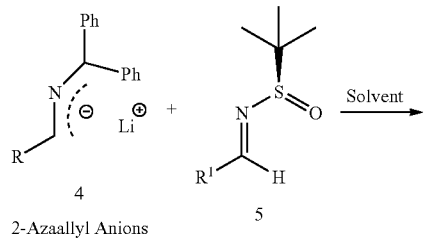

2-Azaallyl Anions (b) condensing 2-azaallyl anion of formula (4) with a compound of formula (5) in a solvent to produce vicinal diamines of formula (1),

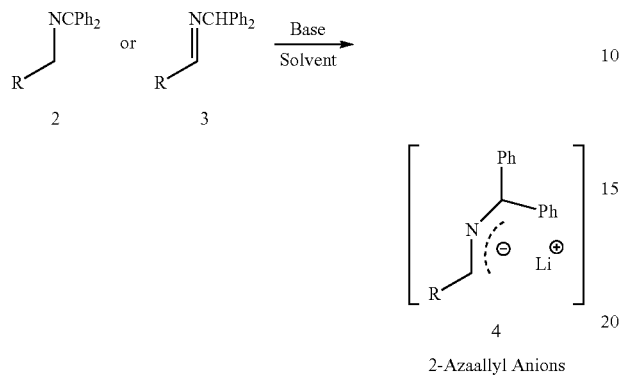

2-Azaallyl Anions

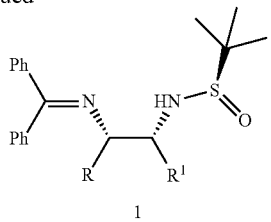

1 wherein, R and $R_1$ is independently selected from H, $C_1$-$C_{10}$ linear or branched or cyclic alkyl, substituted or unsubstituted aryl, ester, ether, hetero aryl, halo, haloalkyl.

2. The process according to claim 1, wherein solvent(s) used in step (a) and (b) is selected from an ether; alcohol; halogenated; ketone solvent; aprotic solvent such as acetonitrile, N,N-dimethyl formamide (DMF), N,N-dimethyl acetamide, dimethylsulfoxide (DMSO) and N-methylpyrrolidone (NMP); an aromatic solvent; water or a mixture thereof.

3. The process according to claim 1, wherein in step (a) and step (b), the solvent is an ether solvent selected from the group consisting of tetrahydrofuran, cyclopentyl methyl ether, 2-methyltetrahydrofuran and diethyl ether.

4. The process according to claim 1, wherein in step (a) the base is selected from potassium hydride (KH), potassium tert-butoxide (tert-BuOK), sodium amide ($NaNH_2$), sodium hexamethyldisilazide (NaHMDS) or a lithium amide base.

5. The process according to claim 1, wherein in step (a) the base is a lithium amide base selected from the group consisting of lithium diethylamide, lithium diisopropylamide (LDA), lithium pyrrolidinamide, lithium piperidinamide, lithium isopropylcyclohexylamide, lithium tetramethylpiperidide (LiTMP) and lithium hexamethyl disilazide (LiHMDS).

6. The process according to claim 1, wherein step (a) is carried out at temperature in the range of −70° C. to −90° C.

* * * * *